United States Patent [19]

Ford et al.

[11] Patent Number: 4,618,716

[45] Date of Patent: Oct. 21, 1986

[54] PREPARATION OF POLYETHYLENE POLYAMINES FROM 2-AMINOETHYL SULFURIC ACID

[75] Inventors: Michael E. Ford, Center Valley; Thomas A. Johnson, Orefield, both of Pa.

[73] Assignee: Air Products and Chemicals, Inc., Allentown, Pa.

[21] Appl. No.: 796,472

[22] Filed: Nov. 8, 1985

[51] Int. Cl.$^4$ ............................................. C07C 85/02
[52] U.S. Cl. ................................................... 564/469
[58] Field of Search ......................................... 564/469

[56] References Cited

U.S. PATENT DOCUMENTS 4,430,513  2/1984  Homeier .............................. 564/469

FOREIGN PATENT DOCUMENTS 785635  10/1977  South Africa ...................... 556/469

Primary Examiner—Paul F. Shaver
Attorney, Agent, or Firm—Russell L. Brewer; E. Eugene Innis; James C. Simmons

[57] ABSTRACT

This invention relates to a process for producing linear polyethylene polyamines. In the process ammonia or an ethylene polyamine is reacted with 2-aminoethyl sulfuric acid to form a higher polyethylene polyamine salt. This salt is subsequently neutralized with a base liberating the free polyethylene polyamine. This product can be recovered from the reaction mixture by filtration and the product polyethylene polyamine purified by distillation.

8 Claims, No Drawings

4,618,716

PREPARATION OF POLYETHYLENE POLYAMINES FROM 2-AMINOETHYL SULFURIC ACID

TECHNICAL FIELD

This invention relates to the preparation of polyethylene polyamines.

BACKGROUND OF THE INVENTION

Polyethylene polyamines are widely known and have general utility as corrosion inhibitors in coolants and lubricant formulations and have utility as coagulants or flocculants for the agglomeration of suspended solids from liquid solutions or slurries. They also have utility in formulating plasticizers and antioxidants for polymers. The linear, as opposed to the cyclic, polythylene polyamines have greater utility for these applications and examples of such linear polyethylene polyamines including diethylenetriamine, triethylenetetramine, tetraethylenepentamine and pentaethylenehexamine.

There have been two standard routes to the preparation of polyethylene polyamines, one being through the chloride route wherein ethylene dichloride is reacted with ammonia or a diamine to produce the polyethylene polyamine and the second has been through the reaction of ethanolamine and ethylenediamine. One of the major disadvantages of the chloride process is that it involves the use of a corrosive halogen-containing starting material. A byproduct of the process is that it generates corrosive hydrochloric acid, vinyl chloride and toxic mustards in the process.

The following patents are representative of processes involving the preparation of polyethylene polyamines from ethanolamine and ethylenediamine.

U.S. Pat. Nos. 4,036,881; 4,394,524; and 4,503,253 show the use of various phosphorus containing catalysts such as phosphoric acid on silica and rare earth metal hydrogen phosphates such as lanthanum hydrogen phosphate.

U.S. Pat. No. 4,316,841 shows the manufacture of polyethylene polyamines through reforming of polyethylene polyamines using a phosphorus catalyst.

U.S. Pat. No. 4,314,083 shows the utilization of the salt of nitrogen or sulfur containing substance as a catalyst.

U.S. Pat. No. 4,362,886 shows the use of arsenic, antimony, or bismuth as a catalyst. p U.S. Pat. No. 4,399,308 shows the use of a Lewis acid halide for preparing polyethylene polyamines.

U.S. Pat. No. 2,364,278 and South African Pat. No. 785,635 disclose processes for the manufacture of polyethylene polyamines by reacting 2-aminoethyl sulfuric acid with ammonia or amine in the presence of alkali metal hydroxide.

SUMMARY OF THE INVENTION

This invention relates to a process for producing polyethylene polyamines in high conversion and high selectivity through the reaction of 2-aminoethyl sulfuric acid with a nitrogen compound. In this process ammonia or a polyethylene polyamine having primary and/or secondary amine groups is reacted with 2-aminoethyl sulfuric acid under conditions sufficient to effect reaction thereof and form a polyethylene polyamine salt. The salt then is converted to the free amine through the addition of a neutralizing agent; e.g., ammonia or an alkali metal hydroxide. The free polyethylene polyamine is liberated from the reaction product by filtration and the product distilled to separate the polyethylene polyamines into its components.

Some of the advantages associated with this process include an ability to produce polyethylene polyamines in high selectivity and high conversion optionally without the need for performed ethylenediamine as a reactant;

an ability to produce ethylenediamine and higher polyethylene polyamines in high selectivity, as compared to other processes;

an ability to selectively produce particular ethylene amines;

a process which is free from extremely corrosive components requiring expensive equipment; and the elimination of toxic ethylene imine from the process through the 2-step synthesis of polyethylene polyamines.

DETAILED DESCRIPTION F THE INVENTION

This invention relates to the preparation of linear polyethylene polyamines, such as diethylenetriamine, triethylenetetramine, tetraethylenepentamine, and pentaethylenehexamine. Very few cyclic polyamines such as piperazine, aminoethylpiperazine, bis(aminoethyl) piperazine, piperazinoethylenediamine, aminoethyl bis-(aminoethyl) piperazine, or aminoethylpiperazinoethylethylenediamine are produced.

In the process 2-aminoethyl sulfuric acid is reacted with ammonia or a polyethlene polyamine such as ethylenediamine, diethylenetriamine, or triethylenetetramine in the presence of a solvent, such as water or alcohol. The 2-aminoethyl sulfuric acid adds a 2-aminoethyl group to the ammonia or polyethylene polyamine to form the polyamine salt. The amine can then be liberated from the salt.

The reaction for preparing polyethylene polyamines in high selectivity is carried out by reacting the ammonia or polyethylene polyamine with 2-aminoethyl sulfuric acid at temperatures from about 80° to 250° C. Preferably the temperature will range from about 110° to 200° C. as high temperatures may tend to increase the production of cyclic materials. Pressures used for the reaction generally range from about atmospheric to 1000 psig and reaction times will range from a low of about ¼ minute to 24 hours.

Reaction times are closely related to the reaction temperatures and pressures used. High temperatures usually generate high pressures and reaction times can be short whereas low temperatures and pressures require longer times. Usually equipment dictates a range of conditions and product slate dictates residence time.

The synthesis of noncyclic, linear polyethylene polyamines is enhanced through the utilization of the 2-aminoethyl sulfuric acid which is a mono-alkylating agent. Since 2-aminoethyl sulfuric acid is internally protonated, the amino group exists as an ammonium salt. This structure favors reaction with ammonia or a polyethylene polyamine rather than self-condensation. In contrast, reactants utilized by the prior art are more apt to form cyclic polyamines. Ethylene dichloride is bifunctional, and the bifunctional nature of the reactant increases the probability of formation of cyclic polyethylene amines. Ethanolamine readily dimerizes to form aminoethylethanolamine, which subsequently cyclizes to form piperazine and higher cyclic polyethylene amines. The mon-alkylating nature of 2-aminoethylhydrogen sulfate makes it impossible to produce cyclic amines by reaction of ammonia or a polyethylene polyamine with 2-aminoethyl hydrogen sulfate. In order to produce cyclic amines under the conditions of this process 2-aminoethyl sulfuric acid must react with itself to form a chain-extended alkylating derivative. This chain-extended derivative of 2-aminoethyl hydrogen sulfate is the only material which can form cyclics. To minimize the production of chain-extended 2-aminoethyl sulfuric acid, i.e., aminoethylated 2-aminoethyl sulfuric acid, the mole ratio of ammonia, ethylenediamine, or polyethylene polyamine is maintained at a level greater than 1:1. Typically the range will be from about 1—30:1 and preferably 2—12:1 moles ammonia or ethylene polyamine per mole of 2-aminoethyl sulfuric acid.

Under the conditions recited the reaction of ammonia or ethylene polyamine with 2-aminoethyl sulfuric acid results in the production of a polyethylene polyamine sulfate salt. This product then can be converted to the free polyethylene polyamine by neutralization with a base, e.g. an alkali metal hydroxide such as sodium or potassium hydroxide; lime or ammonia. In contrast to a procedure used in the pior art the addition of alkali metal hydroxide is made after the formation of the polyethylene polyamine salt and not prior to the polyamine reaction. The in situ conversion of polyethylene polyamine salts, in the presence of free aminoethyl hydrogen sulfate, tends to increase the amount of cyclics and reduce conversion. Another problem associated with the in situ addition of alkali metal hydroxide is the generation of toxic ethylene imine.

Neutralization of the polyethylene polyamine salts is accomplished by the addition of stoichiometric quantities of alkali metal hydroxide, ammonia or other base to the reaction mixture for producing the sulfate salt and polyethylene polyamines. The free polyethylene polyamine product can be recovered from the reaction mixture by filtration. Upon separation from the sulfate salt the polyethylene polyamine product can be separated into its components by distillation.

The following examples are provided to illustrate preferred embodiments of the invention and to facilitate understanding of the procedure for manufacturing polyethylene polyamines.

EXAMPLE 1

Reaction of 2-aminoethyl hydrogen sulfate with ethylenediamine

A round bottomed flask fitted with a thermometer and magnetic stirrer was charged with 30 g of 2-aminoethyl hydrogen sulfate (AES), 30 g of ethylenediamine (EDA) and 2 g biphenyl (internal standard) (mole ratio EDA/AES about 2.4:1). The mixture was heated to 100° C. where upon the reaction mixture appeared homogeneous and a sample (I) was withdrawn. The reaction mixture was subsequently heated to reflux (125° C.) and maintained at reflux for 2 hours. After cooling, a sample II was withdrawn.

Samples I and II were analyzed by HPLC after converting the amine products to m-toluamides with m-toluoyl chloride in aqueous sodium hydroxide solution. The results of the analysis are shown in Table I.

The following abbreviations have been used in the Examples.

AES—Aminoethylsulfuric acid
EDA—Ethylenediamine
MELA—Monoethanolamine
AEEA—Aminoethylethanolamine
PIP—Piperazine
AEP—N(2-aminoethyl)piperazine
DETA—Diethylenetriamine
TAEA—Tris(2-aminoethyl)amine
TETA—Triethylenetetramine (linear isomer only)
BAEP—Bis(2-aminoethyl)piperazine
PEEDA—(2-Piperazinoethyl)ethylenediamine
AETETA—N-(2-aminoethyl)tris(2-aminoethyl)amine
TEPA—Tetraethylenepentamine (linear isomer only)
AEBAEP—N-(2-aminoethyl)bis(2-aminoethyl)—piperazine
AEPEEDA—N'—(2-aminoethyl)—N—(2-piperazinoethyl)ethylenediamine
PEHA—Pentaethylenehexamine
HPLC—High Peformance Liquid Chromatography

TABLE I

| | (Normalized Weight %) | |
|---|---|---|
| | Sample I | Sample II |
| EDA | 100 | 73.00 |
| PIP | 0 | 2.00 |
| DETA | 0 | 18.52 |
| TETA | 0 | 3.97 |
| TEPA | 0 | Trace |
| AEEA | 0 | 2.48 |

Sample I shows that none of the ethylenediamine had been converted at 100° C. within the reaction time stated but when the reactor contents were heated to 125° C. ethylenediamine was alkylated to produce higher molecular weight polyethylene polyamines. Some, although minimal, cyclic amine was produced showing that some AES had reacted with itself.

EXAMPLE 2

Reaction of 2-aminoethyl hydrogen sulfate with ammonia

A 300 ml stirred autoclave was charged with 70.5 g (0.5 mole) 2-aminoethyl hydrogen sulfate (AES), 50.0 g triethyleneglycol dimethyl ether (solvent), 51.0 g (3.0 mole) anhydrous ammonia and 3.0 g biphenyl (internal standard). This mixture was heated at 200° C. (970 psig) for 3 hours. The charge was cooled to 100° C. and 100 ml, 50% aqueous methanol was added. A sample of the charge was taken for analysis. This sample was derivatized with m-toluoyl chloride and analyzed by HPLC.*
The results are shown in Table II.

*HPLC method used for this analysis detects only linear polyethylene plyamines and piperazine. Polyamines containing tertiary amino groups such as tris(aminoethyl)amine and aminoethylpiperazine are retained on the chromatography column and thereby are not detected. Further, unreacted AES is not detected by this method, thus the conversion is not known for this experiment.

TABLE II

| Component | Wt. (g) | Equiv. AES | % Yield** |
|---|---|---|---|
| EDA | 4.97 | .0828 | 16.56 |
| PIP | 1.36 | .0316 | 6.32 |
| DETA | 4.03 | .0783 | 15.66 |
| MELA | .72 | .0118 | 2.36 |
| TETA (Linear) | 2.26 | .0464 | 9.28 |
| AEEA | .70 | .0137 | 2.74 |
| TEPA (Linear) | 2.08 | .0440 | 8.80 |
| PEHA | 1.18 | .0257 | 5.14 |
| | | .3343 | 66.86 |

**Yield (Mole %) Based on AES Charged

The data shows high conversion of ammonia and AES to linear polyethylene polyamines. It also shows the process has the ability to produce a multitude of linear polyethylene polyamines from ammonia e.g., DETA, TETA and TEPA in one step without separating the intermediate ethyleneamines. In contrast, the prior art process of producing polyethylene polyamines from monoethanolamine, ethylenediamine and ammonia requires the additional step of generating ethylenediamine.

EXAMPLE 3

Reaction of aqueous ammonia with 2-aminoethylhydrogen sulfate in continuous reactor mode An aqueous solution of 2-aminoethyl hydrogen sulfate, 2.5M, and ammonia, 18.24M, was pumped through a 25 foot length of ¼" stainless steel tubing at a rate of 1.88/ml/min. A back pressure regulator at the end of the tube reactor was set at 500 psig. The tube reactor was immersed in an oil bath heated to 150° C. A second pump was used to dilute the reactor effluent with water at 3.95 ml/min just before it reached the back pressure regulator to prevent salts from precipitating. The reaction product was collected at the back pressure regulator exit. The product stream was analyzed by liquid chromatography after being derivatized with m-toluoyl chloride. Only piperazine and linear polyethylene polyamines can be analyzed by this procedure.

The conversion of AES was not measured in this experiment.

The yield of linear polyethlene polyamines was 72% in this expriment. The remainder was composed of unconverted AES and branched plus cyclic polyamines. As in Example 2 ammonia was converted to ethylenediamine and higher polyethylene polyamines but on a continuous basis. Table III sets forth these results.

TABLE III

| | Analysis | |
|---|---|---|
| | Conc. (Mole/Liter)* | Yield** |
| EDA | .895 | 36.8 |
| DETA | .373 | 25.0 |
| TETA | .069 | 8.3 |
| TEPA | .018 | 2.9 |
| PIP | .065 | 5.2 |

*Corrected for Post Reactor Dilution

**Yield (Mole %) = $\frac{\text{Ethylene Equivalents}}{\text{Moles AES fed}} \times 100$

EXAMPLE 4

A round bottomed flask fitted with a condenser was charged with 2-aminoethyl hydrogen sulfate, 35.27 g (0.25 mole), and ethylenediamine, 63.33 g (1.05 moles). The mixture was stirred and heated to reflux (125° C.). A sample was withdrawn after 2 hours and analyzed as in Example 3. Analysis of residual 2-aminoethyl hydrogen sulfate was not carried out, thus the conversion was not known but was believed to be low. Table IV sets forth these results.

TABLE IV

| | Analysis | | |
|---|---|---|---|
| | Wt. (g) | Moles | Yield (Mole %)* |
| EDA | 53.2 | .887 | — |
| DETA | 7.79 | .0756 | 30.2 |
| TETA | .65 | .0045 | 3.6 |

*Based on AES Charged

The results show that at low conversion and at low temperature one can minimize the amount of higher polyethylene polyamine production and limit alkylation to the next additional ethylene chain. This is advantageous from a manufacturing point of view since other processes typically result in a more diverse product slate.

EXAMPLE 5

Reaction of 2-aminoethyl hydrogen sulfate with ethylene diamine in batch mode—water added A round bottomed flask was charged with 2-aminoethyl hydrogen sulfate, 35.28 g (0.250 mole), ethylenediamine, 60.45 g (1.006 mole) and water, 18.28 g (1.015 mole). Through the water jacket around the flask was circulated hot oil which maintained the reaction temperature at 119° C. for the duration of the experiment (6 hours). The product was analyzed by liquid chromatography as in Example 3. In addition, the amount of sulfate generated was analyzed by a standard sulfate method using BaCl$_2$. (A mole of sulfate is generated for each mole of 2-aminoethyl hydrogen sulfate reacted).

18.4% of converted AES produced materials not detectable by liquid chromatographic analysis. Table V sets forth the results.

TABLE V

| | Analysis | | | |
|---|---|---|---|---|
| | Wt. (g) | Moles | AES Conv.* | Yield*** |
| EDA | 28.81 | .480 | — | |
| DETA | 13.11 | .127 | 50.8 | 67.7 |
| TETA | 1.49 | .010 | 8.0 } 61.2 | 10.7 |
| TEPA | .30 | .002 | 2.4 | 3.2 |
| AES | 8.82 | .063 | 75.0** | — |
| % of AES Accounted For = 81.6 | | | | |

*AES Conv. = Amount of AES Converted to Each Product
**Total Mole % AES Reacted
***Yield of Each Component (Mole %) Based on Converted AES

EXAMPLE 6

Reaction of diethylenetriamine with 2aminoethyl hydrogen sulfate

A 1 liter 3 necked round bottomed flask was charged with diethylenetriamine, 154.5 (1.5 moles), 2-aminoethyl hydrogen sulfate, 70.5 g (0.5 mole) and water, 36.0 g (2.0 moles) and heated at reflux with stirring over night. After cooling, 50% aqueous NaOH, 80 g (1.0 mole) was added and stirred for 30 minutes. The mixture was then diluted with 95% ethanol, 350 ml; and heated at 80°-85° C. for 30 minutes while stirring. After cooling to room temperature the precipitated sodium sulfate was removed by filtration. The filter cake was washed with an additional portion of 95% ethanol, 350 ml. The filter cake after drying weighed 69.9 g (0.49 mole).

The combined filtrate and washing was rotary evaporated at room temperature at reduced pressure (water aspirator). The residue was then distilled after fitting the flask with a vacuum jacketed 6 inch long Vigreux column. Table VI describes the distillation conditions and product composition.

TABLE VI

DISTILLATION CONDITIONS AND PRODUCT COMPOSITION

| Fract. # | Head Tem.* °C. | Pres. mm Hg | Wt. g | DETA | TETA*** | TETA | TEPA*** | TEPA | AEP | UKS** |
|---|---|---|---|---|---|---|---|---|---|---|
| 1 | 100 | 760 | 60.06 | 3.27 | | | | | | |
| 2 | 100 | 760 | 6.89 | 4.51 | | | | | | |
| 3 | 102 | 17 | 68.88 | 68.88 | | | | | | |
| 4 | 101 | 17 | 20.15 | 19.82 | | | | | .38 | |
| 5 | 145 | 17 | 5.80 | 4.92 | .39 | | | | .21 | .28 |
| 6 | 155 | 17 | 41.48 | | 4.01 | 34.92 | | | | 2.57 |
| 7 | | 17 | 8.70 | | .24 | 1.20 | 4.49 | 2.79 | | |
| X**** | | | 513.86 | 7.27 | | | | | | |
| Residue | | | 8.15 | | | | .14 | .91 | | 7.11 |
| Totals | | | | 108.67 | 4.64 | 36.12 | 4.63 | 3.70 | .59 | 9.96 |

*Maximum head temperature reached.
**Polyamines of undetermined structure.
***Branched Isomer
****Distillate from rotary evaporation.

The results show a high production of TETA, the next polyethylene polyamine in the chain, with little branched and cyclic amine production.

The mass balance for this experiment was 95.6 %. The yield of each component with respect to 2-aminoethyl hydrogen sulfate charged (0.50 mole) is shown below:

| CMPD | Wt. (g) | AES Equiv. | % Yield |
|---|---|---|---|
| TETA'S | 43.61 | .299 | 59.7 |
| TEPA'S | 8.32 | .088 | 17.6 |
| HVYS* | 7.11 | .092 | 18.4 |
| AEP | .54 | .004 | .8 |
| Total | | .483 | 96.6 |

*Assumed to be PEHA'S

EXAMPLE 7

Comparative Example A

This experiment was carried out to determine the effect of added sodium hydroxide during the alkylation of ammonia or ethyleneamine as disclosed by South African Pat. No. 785,635 and U.S. Pat. No. 2,364,178. In comparative Example A the procedure of Example 5 was repeated except that of 80 gm of 25% (w/w) aqueous sodium hydroxide (0.50 mole sodium hydroxide) were included in the reaction medium. As stated the South African and U.S. patents showed the reaction carried out in the presence of base. The product was analyzed by $^{13}$C NMR.

Assignments were made by comparison of the spectrum with $^{13}$C NMR specific of known compounds. Conversion of AES was moderate (67%); diethylenetriamine was obtained in high selectivity (82%, based on total polyamine product; see Tables VII and VIII). In contrast to the product slate obtained in Example 5, piperazine and aminoethylethanolamine were formed. These products, a cyclic polyamine and an aminoalcohol, respectively, represent yield losses of AES relative to formation of commercially desired noncyclic polyethylene polyamines. Although selectivity to total noncyclics was high, only diethylenetriamine (and no higher noncyclic polyamines) could be detected. Therefore, the product of this experiment had a lower average molecular weight than that of Experiment 5. (This data and analysis technique shows somewhat different results than reported in the prior art.)

Comparative Example B

The process of Example 1 of South African patent was repeated using similar mole ratios to provide a sample of the polyethylene polyamine product for analysis by $^{13}$C NMR. Conversion of AES to polyethylene polyamines was complete. However, cyclic polyamines predominated (59 molar percent selectivity; see Tables VII and VIII).

TABLE VII

| | Polyamines from EDA/AES/Sodium Hydroxide | | | | |
|---|---|---|---|---|---|
| Comparative | EDA/AES/ | Conversion | Selectivity (%) | | |
| Example | NaOH | (%) | NC | Cyclics | AEEA |
| A | 4/1/2 | 67 | 82 | 11 | 7 |
| B | 0.05/1/2 | 109 | 41 | 59 | 0 |

TABLE VIII

| | Product Slate | |
|---|---|---|
| | Product (%)$^a$ | |
| Component | 4/1/2 | 0.05/1/2 |
| PIP | 11.0 | 28.5 |
| DETA | 81.8 | 29.2 |
| AEP | $^b$ | 9.9 |
| NCTETA | $^b$ | 11.7 |
| HVY CYCLICS | $^b$ | 20.7 |
| AEEA | 7.2 | 0.0 |
| | 100.0 | 100.0 |

$^a$Expressed on a mole percent basis.
$^b$Not detected.

The product slate obtained when the reaction of ethylenediamine and AES is carried out in the presence of base is quite different than that obtained when the reaction is carried out as a two step process. Although not intending to be bound by theory, it is believed that strong based added prior to polyamine formation reacts with the aminoethyl hydrogen sulfate. The ammonium group of aminoethyl hydrogen sulfate, a very weak nucleophile which is stable under reaction conditions, is converted into an amine group. Owing to its free lone pair of electrons, the amine is a strong nucleophile, and can displace sulfate from additional aminoethyl sulfuric acid to form a chain-extended intermediate and ultimately cyclic polyethylene polyamines. In contrast, when base is added at the conclusion of the reaction, its only effect is to liberate product noncyclic polyethylene polyamines from their sulfate salts. Therefore, less cyclic material is obtained.

Comparative Example B is important to show the effect of the mole ratio of amine to AES on product slate. When the mole ratio is less than 1:1 there is an ability to produce a substantial amount of cyclics particularly when the reaction is carried out in the presence of base.

What is claimed is:

1. In a process for producing polyethylene polyamines utilizing 2-aminoethyl sulfuric acid as a reactant, the improvement for enhancing the production of polyethylene polyamines with high selectivity to linear polyethylene polyamines which comprises:

reacting ammonia or an ethyleneamine with 2-aminoethyl sulfuric acid under conditions sufficient to form a higher polyethylene polyamine salt, neutralizing the higher polyethylene polyamine salt under conditions for forming the free amine; and recovering said free higher polyethylene polyamine.

2. The process of claim 1 wherein said neutralization of said polyethylene polyamine salt is effected by the addition of ammonia or alkali metal hydroxide.

3. The process of claim 2 wherein the free polyethylene polyamine is separated from the reaction mixture, after neutralization, by filtration.

4. The process of claim 2 wherein the reaction temperature is from 80°–250° C.

5. The process of claim 4 wherein the pressure utilized from about atmospheric to 1000 psig.

6. The process of claim 5 wherein the molar ratio of ammonia or ethyleneamine to 2-aminoethyl sulfuric acid is from 2–12:1.

7. The process of claim 6 wherein said ethyleneamine is ethylene diamine and it is reacted with 2-aminoethyl sulfuric acid to produce polyethylene polyamines.

8. The process of claim 6 wherein ammonia is reacted with 2-aminoethyl sulfuric acid.

* * * * *